United States Patent
Liversidge et al.

(10) Patent No.: US 7,910,577 B2
(45) Date of Patent: Mar. 22, 2011

(54) INJECTABLE NANOPARTICULATE OLANZAPINE FORMULATIONS

(75) Inventors: Gary Liversidge, West Chester, PA (US); Scott Jenkins, Downingtown, PA (US); Elaine Merisko Liversidge, West Chester, PA (US)

(73) Assignee: Elan Pharma International Limited, Athlone, County Westmeath (IE)

( * ) Notice: Subject to any disclaimer, the term of this patent is extended or adjusted under 35 U.S.C. 154(b) by 1167 days.

(21) Appl. No.: 11/274,887

(22) Filed: Nov. 16, 2005

(65) Prior Publication Data

US 2006/0154918 A1    Jul. 13, 2006

Related U.S. Application Data

(60) Provisional application No. 60/628,748, filed on Nov. 16, 2004.

(51) Int. Cl.
  *A61K 31/55* (2006.01)
  *A01N 43/00* (2006.01)
  *A01N 43/46* (2006.01)
  *C07D 243/10* (2006.01)

(52) U.S. Cl. ........ 514/220; 977/902; 977/904; 977/905; 977/906; 977/915; 540/557

(58) Field of Classification Search .................. None
  See application file for complete search history.

(56) References Cited

U.S. PATENT DOCUMENTS

| | | | |
|---|---|---|---|
| 4,783,484 A | 11/1988 | Violante et al. | |
| 4,826,689 A | 5/1989 | Violanto et al. | |
| 4,997,454 A | 3/1991 | Violante et al. | |
| 5,145,684 A | 9/1992 | Liversidge et al. | |
| 5,229,382 A | 7/1993 | Chakrabarti et al. | |
| 5,298,262 A | 3/1994 | Na et al. | |
| 5,302,401 A | 4/1994 | Liversidge et al. | |
| 5,336,507 A | 8/1994 | Na et al. | |
| 5,340,564 A | 8/1994 | Illig et al. | |
| 5,346,702 A | 9/1994 | Na et al. | |
| 5,352,459 A | 10/1994 | Hollister et al. | |
| 5,399,363 A | 3/1995 | Liversidge et al. | |
| 5,429,824 A | 7/1995 | June | |
| 5,470,583 A | 11/1995 | Na et al. | |
| 5,494,683 A | 2/1996 | Liversidge et al. | |
| 5,510,118 A | 4/1996 | Bosch et al. | |
| 5,518,187 A | 5/1996 | Bruno et al. | |
| 5,518,738 A | 5/1996 | Eickhoff et al. | |
| 5,534,270 A | 7/1996 | De Castro | |

(Continued)

FOREIGN PATENT DOCUMENTS

EP    0 499 299 B1    8/2000

(Continued)

OTHER PUBLICATIONS

Tohen, Mauricio et al.; Efficacy of Olanzapine and Olanzapine-Fluoxetine Combination in the Treatment of Bipolar I Depression,2003, American Medical Association, Arch Gen Psychiatry, vol. 60, Nov. 2003, pp. 1079-1088.*

(Continued)

*Primary Examiner* — Yvonne L Eyler
*Assistant Examiner* — Ivan Green
(74) *Attorney, Agent, or Firm* — Fox Rothschild LLP

(57) ABSTRACT

Described are injectable formulations of nanoparticulate olanzapine that produce a prolonged duration of action upon administration, and methods of making and using such formulations. The injectable formulations comprise nanoparticulate olanzapine.

17 Claims, 5 Drawing Sheets

Olanzapine crystals prior to particle size reduction

U.S. PATENT DOCUMENTS

| | | | |
|---|---|---|---|
| 5,543,133 A | 8/1996 | Swanson et al. |
| 5,552,160 A | 9/1996 | Liversidge et al. |
| 5,560,931 A | 10/1996 | Eickhoff et al. |
| 5,560,932 A | 10/1996 | Bagchi et al. |
| 5,565,188 A | 10/1996 | Wong et al. |
| 5,569,448 A | 10/1996 | Wong et al. |
| 5,571,536 A | 11/1996 | Eickhoff et al. |
| 5,573,783 A | 11/1996 | Desieno et al. |
| 5,580,579 A | 12/1996 | Ruddy et al. |
| 5,585,108 A | 12/1996 | Ruddy et al. |
| 5,587,143 A | 12/1996 | Wong |
| 5,591,456 A | 1/1997 | Franson et al. |
| 5,622,938 A | 4/1997 | Wong |
| 5,637,584 A | 6/1997 | Larsen |
| 5,662,883 A | 9/1997 | Bagchi et al. |
| 5,665,331 A | 9/1997 | Bagchi et al. |
| 5,703,232 A | 12/1997 | Bunnell et al. |
| 5,718,388 A | 2/1998 | Czekai et al. |
| 5,718,919 A | 2/1998 | Ruddy et al. |
| 5,736,541 A | 4/1998 | Bunnell et al. |
| 5,741,522 A | 4/1998 | Violante et al. |
| 5,747,001 A | 5/1998 | Wiedmann et al. |
| 5,776,496 A | 7/1998 | Violante et al. |
| 5,834,025 A | 11/1998 | De Garavilla et al. |
| 5,862,999 A | 1/1999 | Czekai et al. |
| 6,020,487 A | 2/2000 | Bunnell et al. |
| 6,045,829 A | 4/2000 | Liversidge et al. |
| 6,068,858 A | 5/2000 | Liversidge et al. |
| 6,153,225 A | 11/2000 | Lee et al. |
| 6,165,506 A | 12/2000 | Jain et al. |
| 6,221,400 B1 | 4/2001 | Liversidge et al. |
| 6,251,895 B1 | 6/2001 | Larsen et al. |
| 6,264,922 B1 | 7/2001 | Wood et al. |
| 6,267,989 B1 | 7/2001 | Liversidge et al. |
| 6,270,806 B1 | 8/2001 | Liversidge et al. |
| 6,316,029 B1 | 11/2001 | Jain et al. |
| 6,375,986 B1 | 4/2002 | Ryde et al. |
| 6,428,814 B1 | 8/2002 | Bosch |
| 6,431,478 B1 | 8/2002 | Reed et al. |
| 6,432,381 B2 | 8/2002 | Liversidge et al. |
| 6,582,285 B2 | 6/2003 | Czekai et al. |
| 6,592,903 B2 | 7/2003 | Ryde et al. |
| 6,617,321 B2 | 9/2003 | Allen et al. |
| 6,656,504 B1 | 12/2003 | Bosch et al. |
| 6,742,734 B2 | 6/2004 | Reed et al. |
| 6,745,962 B2 | 6/2004 | Reed et al. |
| 6,811,767 B1 | 11/2004 | Bosch et al. |
| 6,906,062 B2 | 6/2005 | Chhabada et al. |
| 6,908,626 B2 | 6/2005 | Cooper et al. |
| 2002/0012675 A1 | 1/2002 | Jain et al. |
| 2002/0119916 A1* | 8/2002 | Hassan ............... 514/9 |
| 2002/0165225 A1 | 11/2002 | Hamied et al. |
| 2004/0067936 A1 | 4/2004 | Reguri et al. |
| 2004/0198721 A1 | 10/2004 | Dolitzky et al. |
| 2007/0004706 A1 | 1/2007 | Petho et al. |
| 2007/0043021 A1 | 2/2007 | Solomon |

FOREIGN PATENT DOCUMENTS

| | | |
|---|---|---|
| WO | WO 00/53164 | 9/2000 |
| WO | WO 02/098565 A1 | 12/2002 |
| WO | WO 2004/032980 * | 4/2004 |
| WO | WO 2004/032980 A1 | 4/2004 |

OTHER PUBLICATIONS

Love, Raymond C.; Strategies for increasing treatment compliance: The role of long-acting antipsychotics; 2002; American Society of Health-System Pharmacistis; Am J Health-Syst Pharm, vol. 59, Nov. 15, 2002, Supplement 8, pp. S10-S15.*

*The Merck Index*, 10<sup>th</sup> Ed., p. 1106 (Merck & Co., Rahway, NJ, 1983).

* cited by examiner

FIGURE 1: Olanzapine crystals prior to particle size reduction

FIGURE 2: Olanzapine crystals following particle size reduction

FIGURE 3: Olanzapine crystals following particle size reduction

NanoOlanzapine Dog Study

Dosing (IM @ 10mg/kg ~100mg per animal)

NanoOlanzapine Dog Study

Dosing (IM @ 10mg/kg ~100mg per animal)

Dose 10X the daily dose in man & well tolerated

Mean Values for Six Animals

INJECTABLE NANOPARTICULATE OLANZAPINE FORMULATIONS

RELATIONSHIP TO PRIOR APPLICATIONS

This application claims priority under 35 U.S.C. §119(e) to U.S. Provisional Patent Application 60/628,746, filed on Nov. 16, 2004.

BACKGROUND OF THE INVENTION

1. Field of the Invention

The present invention is directed to novel delivery systems for psychotropic agents that ensure better patient compliance and therefore improved therapeutic efficacy and better overall mental health for the patient. More specifically, the present invention comprises injectable nanoparticulate olanzapine formulations having a prolonged duration of action.

2. Background of Invention

A. Background Regarding Olanzapine

Currently there are many drugs available for the treatment of disorders of the central nervous system. Among these drugs is a category known as antipsychotics for treating serious mental conditions such as schizophrenia and schizophreniform illness. The drugs available for such conditions are often associated with undesirable side effects, and there is a need for better products that control or eliminate the symptoms in a safer and more effective way. Furthermore, many patients do not respond or only partially respond to present drug treatment, and estimates of such partial-or non-responders vary between 40% and 80% of those treated.

Since antipsychotics were introduced it has been observed that patients are liable to suffer from drug-induced extra pyramidal symptoms, which include drug-induced Parkinsonism, acute dystonic reactions, akathisia, tardive dyskinesia, and tardive dystonia. The Simpson Angus Scale, Barnes Akathisia Rating Scale, and Abnormal Involuntary Movement Scale (AIMS) are well known scales for assessing extra pyramidal symptoms. The great majority of drugs available for treatment of schizophrenia are prone to produce these extra pyramidal side effects when used at dosages that yield a beneficial effect on the symptoms of the disease. The severity of adverse events and/or lack of efficacy in a considerable number of patients frequently result in poor compliance or termination of treatment.

Many of the drugs are associated with a sedative effect and may also have an undesirable influence on the affective symptoms of the disease, causing depression. In some instances long term use of the drug leads to irreversible conditions, such as the tardive dyskinesia and tardive dystonia referred to above. This, coupled with the fact that many of the patients in need of such drugs are not in full control of their mental faculties, often results in poor patient compliance and diminished therapeutic effect. A dosage form of such a drug having prolonged activity, and therefore requiring less frequent administrations, is highly desirable. This is because such a dosage form would minimize complications caused by patients missing or failing to take a dose.

A widely used and popular anti-psychotic drug useful in the treatment of disorders of the central nervous system is olanzapine, which is commercially available as Zyprexa® (Eli Lilly, Indianapolis, Ind.). Zyprexa® is available in both orally administered tablets and intramuscular injection formulations.

Olanzapine has the chemical name 2-methyl-4-(4-methyl-1-piperazinyl)-10H-thieno[2,3-b][1,5]benzodiazepine ($C_{17}H_{20}N_4S$), a molecular weight of 312.439, and the following chemical structure:

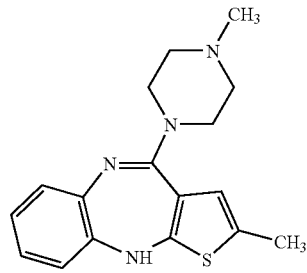

Olanzapine is a yellow crystalline solid which is practically insoluble in water. The compound is disclosed and claimed in U.S. Pat. No. 5,229,382 to Chakrabarti et al., which is incorporated herein by reference.

Olanzapine is an antagonist of dopamine at D-1 and D-2 receptors, and in addition has antimuscarinic, anti-cholinergic properties, and is an antagonist for 5HT-2 receptor sites. The compound also has antagonist activity at noradrenergic alpha-receptors. These properties indicate that the compound is a potential neuroleptic with relaxant, anxiolytic, or anti-emetic properties, and is useful in treating psychotic conditions such as schizophrenia, schizophreniform diseases, and acute mania. At lower doses the compound is indicated for use in the treatment of mild anxiety states.

Olanzapine is a selective monoaminergic antagonist with high affinity binding to the following receptors serotonin $5HT_{2A/2C}$ ($K_I$=4 and 11 nM, respectively), dopamine $D_{1-4}$ ($K_I$=11-31, 25 nM), histamine $H_I$(KI=7 nM), and adrenergic (alpha)$_1$ receptors ($K_I$=nM) $GABA_A$, BZD, and (beta) adrenergic receptors ($K_I$>10 µM).

The mechanism of action of olanzapine, as with other drugs having efficacy in schizophrenia is unknown. However, it has been proposed that this drug's efficacy in schrizophrenia is mediated through a combination of dopamine and serotonin type 2 ($5HT_2$) antagonism. The mechanism of action of olanzapine in the treatment of acute manic episodes associated with Bipolar 1 Disorder is unknown.

Antagonism at receptor other than dopamine and $5HT_2$ with similar receptor affinities may explain some of the other therapeutic and side effect of olanzapine. Olanzapine's antagonism of muscorinic $M_{1-5}$ receptors explains its anticholinergic effects. Olanzapine's antagonism of histamine $H_1$ receptors may explain somnolence observed with this drug. Olanzapine's antagonism of adrenergic (alpha) receptors may explain orthostatic hypotension observed with this drug.

B. Background Regarding Nanoparticulate Drugs

Bioavailability is the degree to which a drug becomes available to the target tissue after administration. Many factors can affect bioavailability including the dosage form and various properties, e.g., dissolution rate of the drug. Poor bioavailability is a significant problem encountered in the development of pharmaceutical compositions, particularly those containing an active ingredient that is poorly soluble in water. Poorly water soluble drugs tend to be unsafe for intravenous administration techniques, which are used primarily in conjunction with fully soluble drug substances.

It is known that the rate of dissolution of a particulate drug can increase with increasing surface area, i.e., decreasing particle size. Consequently, methods of making finely divided drugs have been studied and efforts have been made to control the size and size range of drug particles in pharmaceutical compositions. U.S. Pat. No. 5,145,684 to Liversidge et. al., which is herein incorporated by reference, discloses particles of a drug substance having a non-crosslinked surface stabilizer absorbed on the surface thereof and methods for the preparation thereof. This patent does not teach or suggest nanoparticulate compositions of olanzapine.

Methods of making nanoparticulate compositions are described, for example, in U.S. Pat. Nos. 5,518,187 and 5,862,999, both for "Method of Grinding Pharmaceutical Substances;" U.S. Pat. No. 5,718,388, for "Continuous Method of Grinding Pharmaceutical Substances;" and U.S. Pat. No. 5,510,118 for "Process of Preparing Therapeutic Compositions Containing Nanoparticles." These patents do not describe methods of making nanoparticulate olanzapine.

Nanoparticulate compositions are also described, for example, in U.S. Pat. Nos. 5,298,262 for "Use of Ionic Cloud Point Modifiers to Prevent Particle Aggregation During Sterilization;" U.S. Pat. No. 5,302,401 for "Method to Reduce Particle Size Growth During Lyophilization;" U.S. Pat. No. 5,336,507 for "Use of Charged Phospholipids to Reduce Nanoparticle Aggregation;" U.S. Pat. No. 5,340,564 for "Formulations Comprising Olin 10-G to Prevent Particle Aggregation and Increase Stability;" U.S. Pat. No. 5,346,702 for "Use of Non-Ionic Cloud Point Modifiers to Minimize Nanoparticulate Aggregation During Sterilization;" U.S. Pat. No. 5,352,459 for "Use of Purified Surface Modifiers to Prevent Particle Aggregation During Sterilization;" U.S. Pat. Nos. 5,399,363 and 5,494,683, both for "Surface Modified Anticancer Nanoparticles;" U.S. Pat. No. 5,429,824 for "Use of Tyloxapol as a Nanoparticulate Stabilizer;" U.S. Pat. No. 5,470,583 for "Method of Preparing Nanoparticle Compositions Containing Charged Phospholipids to Reduce Aggregation;" U.S. Pat. No. 5,518,738 for "Nanoparticulate NSAID Formulations;" U.S. Pat. No. 5,552,160 for "Surface Modified NSAID Nanoparticles;" U.S. Pat. No. 5,560,931 for "Formulations of Compounds as Nanoparticulate Dispersions in Digestible Oils or Fatty Acids;" U.S. Pat. No. 5,565,188 for "Polyalkylene Block Copolymers as Surface Modifiers for Nanoparticles;" U.S. Pat. No. 5,569,448 for "Sulfated Non-ionic Block Copolymer Surfactant as Stabilizer Coatings for Nanoparticle Compositions;" U.S. Pat. No. 5,571,536 for "Formulations of Compounds as Nanoparticulate Dispersions in Digestible Oils or Fatty Acids;" U.S. Pat. No. 5,573,783 for "Redispersible Nanoparticulate Film Matrices With Protective Overcoats;" U.S. Pat. No. 5,580,579 for "Site-specific Adhesion Within the GI Tract Using Nanoparticles Stabilized by High Molecular Weight, Linear Poly(ethylene Oxide) Polymers;" 5,585,108 for "Formulations of Oral Gastrointestinal Therapeutic Agents in Combination with Pharmaceutically Acceptable Clays;" U.S. Pat. No. 5,587,143 for "Butylene Oxide-Ethylene Oxide Block Copolymers Surfactants as Stabilizer Coatings for Nanoparticulate Compositions;" U.S. Pat. No. 5,591,456 for "Milled Naproxen with Hydroxypropyl Cellulose as Dispersion Stabilizer;" U.S. Pat. No. 5,622,938 for "Sugar Based Surfactant for Nanocrystals;" U.S. Pat. No. 5,718,919 for "Nanoparticles Containing the R(-)Enantiomer of Ibuprofen;" U.S. Pat. No. 5,747,001 for "Aerosols Containing Beclomethasone Nanoparticle Dispersions;" U.S. Pat. No. 5,834,025 for "Reduction of Intravenously Administered Nanoparticulate Formulation Induced Adverse Physiological Reactions;" U.S. Pat. No. 6,045,829 "Nanocrystalline Formulations of Human Immunodeficiency Virus (HIV) Protease Inhibitors Using Cellulosic Surface Stabilizers;" U.S. Pat. No. 6,068,858 for "Methods of Making Nanocrystalline Formulations of Human Immunodeficiency Virus (HIV) Protease Inhibitors Using Cellulosic Surface Stabilizers;" U.S. Pat. No. 6,153,225 for "Injectable Formulations of Nanoparticulate Naproxen;" U.S. Pat. No. 6,165,506 for "New Solid Dose Form of Nanoparticulate Naproxen;" U.S. Pat. No. 6,221,400 for "Methods of Treating Mammals Using Nanocrystalline Formulations of Human Immunodeficiency Virus (HIV) Protease Inhibitors;" U.S. Pat. No. 6,264,922 for "Nebulized Aerosols Containing Nanoparticle Dispersions;" U.S. Pat. No. 6,267,989 for "Methods for Preventing Crystal Growth and Particle Aggregation in Nanoparticle Compositions;" U.S. Pat. No. 6,270,806 for "Use of PEG-Derivatized Lipids as Surface Stabilizers for Nanoparticulate Compositions;" U.S. Pat. No. 6,316,029 for "Rapidly Disintegrating Solid Oral Dosage Form," U.S. Pat. No. 6,375,986 for "Solid Dose Nanoparticulate Compositions Comprising a Synergistic Combination of a Polymeric Surface Stabilizer and Dioctyl Sodium Sulfosuccinate," U.S. Pat. No. 6,428,814 for "Bioadhesive nanoparticulate compositions having cationic surface stabilizers;" U.S. Pat. No. 6,431,478 for "Small Scale Mill;" U.S. Pat. No. 6,432,381 for "Methods for Targeting Drug Delivery to the Upper and/or Lower Gastrointestinal Tract," U.S. Pat. No. 6,592,903 for "Nanoparticulate Dispersions Comprising a Synergistic Combination of a Polymeric Surface Stabilizer and Dioctyl Sodium Sulfosuccinate," U.S. Pat. No. 6,582,285 for "Apparatus for sanitary wet milling;" U.S. Pat. No. 6,656,504 for "Nanoparticulate Compositions Comprising Amorphous Cyclosporine;" U.S. Pat. No. 6,742,734 for "System and Method for Milling Materials;" U.S. Pat. No. 6,745,962 for "Small Scale Mill and Method Thereof;" U.S. Pat. No. 6,811,767 for "Liquid droplet aerosols of nanoparticulate drugs;" and U.S. Pat. No. 6,908,626 for "Compositions having a combination of immediate release and controlled release characteristics;" all of which are specifically incorporated by reference. In addition, U.S. Patent Application No. 20020012675 A1, published on Jan. 31, 2002, for "Controlled Release Nanoparticulate Compositions," and WO 02/098565 for "System and Method for Milling Materials," describe nanoparticulate active agent compositions, and are specifically incorporated by reference. None of these references describe nanoparticulate compositions of olanzapine.

Amorphous small particle compositions are described, for example, in U.S. Pat. Nos. 4,783,484 for "Particulate Composition and Use Thereof as Antimicrobial Agent;" U.S. Pat. No. 4,826,689 for "Method for Making Uniformly Sized Particles from Water-Insoluble Organic Compounds;" U.S. Pat. No. 4,997,454 for "Method for Making Uniformly-Sized Particles From Insoluble Compounds;" U.S. Pat. No. 5,741,522 for "Ultrasmall, Non-aggregated Porous Particles of Uniform Size for Entrapping Gas Bubbles Within and Methods;" and U.S. Pat. No. 5,776,496, for "Ultrasmall Porous Particles for Enhancing Ultrasound Back Scatter." These references do not describe nanoparticulate olanzapine.

There is a need in the art for nanoparticulate olanzapine formulations which overcome these and other problems associated with prior conventional olanzapine formulations. The present invention satisfies these needs.

SUMMARY OF THE INVENTION

The present invention relates to injectable nanoparticulate olanzapine compositions. The compositions comprise olanzapine and at least one surface stabilizer, which is preferably adsorbed on or associated with the surface of the olanzapine particles. The nanoparticulate olanzapine particles have an effective average particle size of less than about 5 microns. The surface stabilizer is present in an amount sufficient to maintain the olazapine at an effective average particle size that maintains the efficacy of the drug over a period of time, such as about one week or greater than about one week. The nanoparticle size of the olanzapine particles can be manipulated to give the desirable blood profile and duration of action when administered by either intramuscular (IM) or subcutaneous (SC) routes.

Long acting anti-psychotics are preferred, as the patient population treated with such drugs can suffer from poor patient compliance, resulting in diminished therapeutic effect for the administered drug. Drugs requiring multiple daily administration, or even daily administration, are not preferred for this patient population. A simpler dosage form, such as a once-weekly dosage form, can result in dramatically improved patient compliance, and consequently improved quality of life. Advantages and properties of the compositions of the invention are described herein.

Another aspect of the invention is directed to pharmaceutical compositions comprising a nanoparticulate olanzapine composition of the invention. The pharmaceutical compositions preferably comprise olanzapine, at least one surface stabilizer, and at least one pharmaceutically acceptable carrier, as well as any desired excipients.

The invention further discloses a method of making a nanoparticulate olanzapine composition. Such a method comprises contacting olanzapine and at least one surface stabilizer for a time and under conditions sufficient to provide a nanoparticulate olanzapine composition. The one or more surface stabilizers can be contacted with olanzapine either before, preferably during, or after size reduction of the olanzapine.

The present invention is also directed to methods of treatment using the injectable nanoparticulate olanzapine compositions of the invention for, for example, psychotropic therapy and the treatment of central nervous system disorders. In one embodiment of the invention, intramuscular or subcutaneous injection of olanzapine is utilized. The administration of the drug in this manner allows for the formation of an intramuscular or subcutaneous depot of olanzapine which slowly releases the drug into the patient's system over a longer period of time than if administered orally. The period of time over which the drug is released is preferably up to about one week, from about two weeks to about six weeks, and from about two weeks to about twelve weeks. Additional time periods of efficacy are described herein. This allows for improved patient compliance with enhanced therapeutic outcomes. Moreover, injectable formulations of olanzapine result in a significantly shorter response time as compared to oral administration. While current conventional formulations of olanzapine can be formulated for injection (i.e., Zyprexa®), such conventional injectable olanzapine formulations are difficult to prepare due to the low water solubility of the drug.

In psychotropic therapy and the treatment of central nervous system disorders, it is important to provide an olanzapine dosage form that delivers the required therapeutic amount of the drug in vivo and renders the drug bioavailable in a rapid and consistent manner. The nanoparticulate olanzapine formulations of the present invention achieve those goals through the formation of a drug depot, preferably following intramuscular injection. The depot slowly releases the drug into the bloodstream at almost zero order kinetics for about one (1) to about twelve (12) weeks through control of the nanoparticle size of the drug. Different nanoparticle sizes will dissolve at different rates, and will therefore release the drug to the bloodstream from the depot at different release rates.

Both the foregoing general description and the following brief description of the drawings and detailed description are exemplary and explanatory and are intended to provide further explanation of the invention as claimed. Other objects, advantages, and novel features will be readily apparent to those skilled in the art from the following detailed description of the invention.

DETAILED DESCRIPTION OF INVENTION

Figure 1:
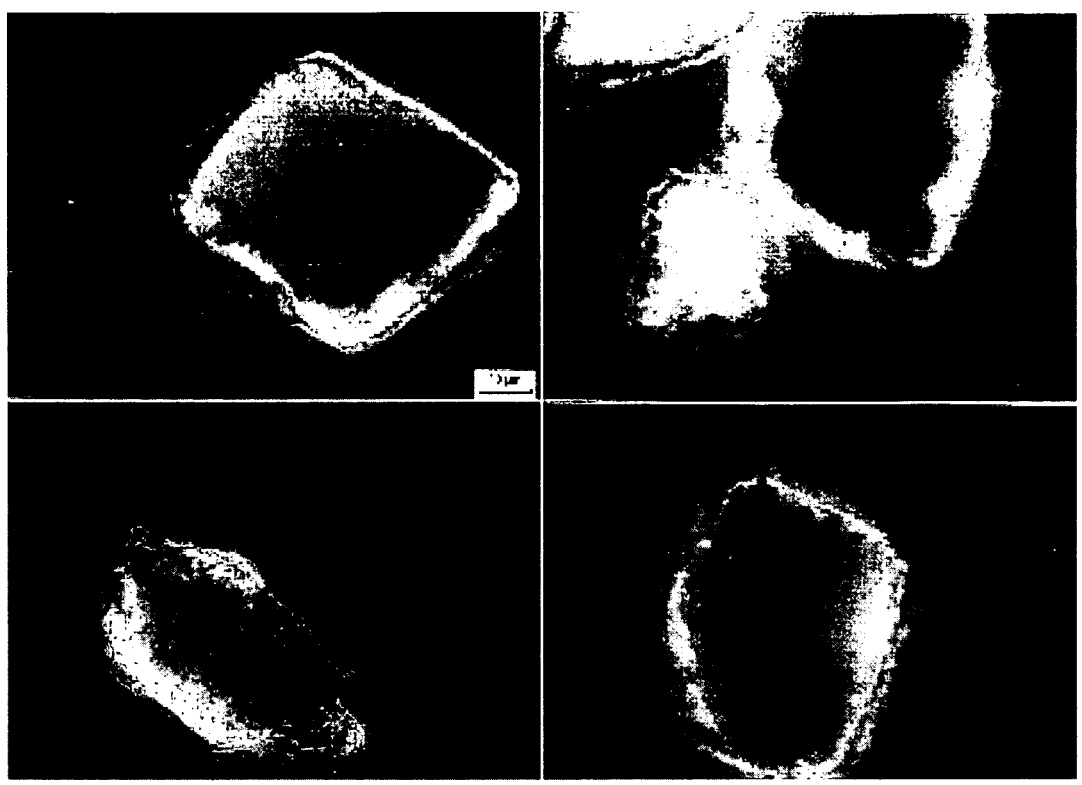
FIG. 1: Shows an electron micrograph of unmilled olanzapine.

The invention provides injectable nanoparticulate olanzapine formulations that can comprise high drug concentrations in low injection volumes, with durations of action that can be controlled to give efficacious blood levels through manipulation of particle size and hence dissolution for periods of about one week or greater.

In other embodiments of the invention, compositions of the invention provide efficacious levels of drug from about one week to about two weeks, from about one week to about three weeks, from about one week to about four weeks, from about one week to about five weeks, from about one week to about six weeks, from about one week to about seven weeks, from about one week to about eight weeks, from about one week to about nine weeks, from about one week to about ten weeks, from about one week to about eleven weeks, from about one week to about twelve weeks, and any combination thereof, such as from about two weeks to about six weeks, from about three weeks to about four weeks, from about three weeks to about seven weeks, etc.

The composition of the invention is administered via injection, such as by intramuscular or subcutaneously, to form a drug depot. The drug depot results in efficacious levels of drug up to about one week or greater.

As taught in U.S. Pat. No. 5,145,684, not every combination of surface stabilizer and active agent will result in a stable nanoparticulate composition. It was surprisingly discovered that stable, injectable, nanoparticulate olanzapine formulations can be made.

The current formulations of olanzapine suffer from the following problems: (1) the poor solubility of the drug results in a relatively low bioavailability; (2) dosing must be repeated several times each day; and (3) a wide variety of side effects are associated with the current dosage forms of the drug.

The present invention overcomes problems encountered with the prior art olanzapine formulations. Specifically, the nanoparticulate olanzapine formulations of the invention may offer the following advantages: (1) a decrease in the frequency of dosing and/or prolonged therapeutic levels of drug following dosing; (2) faster onset of action; (3) smaller doses of olanzapine required to obtain the same pharmacological effect; (4) increased bioavailability; (5) improved performance characteristics for intravenous, subcutaneous, or intramuscular injection, such as higher dose loading and smaller liquid dose volumes; (6) improved pharmacokinetic profiles, such as improved $C_{max}$ and AUC profiles; (7) substantially similar or bioequivalent pharmacokinetic profiles of the nanoparticulate olanzapine compositions when administered in the fed versus the fasted state; (8) bioadhesive olanzapine formulations, which can coat the desired site of application and be retained for a period of time, thereby increasing the efficacy of the drug as well as eliminating or decreasing the frequency of dosing; (9) high redispersibility of the nanoparticulate olanzapine particles present in the compositions of the invention following administration; (10) low viscosity liquid nanoparticulate olanzapine dosage forms can be made; (11) the nanoparticulate olanzapine compositions can be used in conjunction with other active agents; (12) the nanoparticulate olanzapine compositions can be sterile filtered; (13) the nanoparticulate olanzapine compositions are suitable for parenteral administration; and (14) the nanoparticulate olanzapine compositions do not require organic solvents or pH extremes.

A preferred dosage form of the invention is a liquid injectable formulation. However, the composition may also be formulated in a powder or solid for reconstitution prior to injectable administration, such as by lyophilization. The dosage form can be, for example, controlled release dosage form, delayed release dosage form, extended release dosage form, pulsatile release dosage form, mixed immediate release and controlled release dosage form, or a combination thereof.

The present invention is described herein using several definitions, as set forth below and throughout the application.

As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

"Conventional" or "non-nanoparticulate active agent" shall mean an active agent which is solubilized or which has an effective average particle size of greater than about 5 microns. Nanoparticulate active agents as defined herein have an effective average particle size of less than about 5 microns.

"Poorly water soluble drugs" as used herein means those having a solubility of less than about 30 mg/ml, preferably less than about 20 mg/ml, preferably less than about 10 mg/ml, or preferably less than about 1 mg/ml.

As used herein with reference to stable drug particles, 'stable' includes, but is not limited to, one or more of the following parameters: (1) that the olanzapine particles do not appreciably flocculate or agglomerate due to interparticle attractive forces, or otherwise significantly increase in particle size over time; (2) that the physical structure of the olanzapine particles is not altered over time, such as by conversion from an amorphous phase to crystalline phase; (3) that the olanzapine particles are chemically stable; and/or (4) where the olanzapine has not been subject to a heating step at or above the melting point of the olanzapine in the preparation of the nanoparticles of the invention.

'Therapeutically effective amount' as used herein with respect to a drug dosage, shall mean that dosage that provides the specific pharmacological response for which the drug is administered in a significant number of subjects in need of such treatment. It is emphasized that 'therapeutically effective amount,' administered to a particular subject in a particular instance will not always be effective in treating the diseases described herein, even though such dosage is deemed a 'therapeutically effective amount' by those skilled in the art. It is to be further understood that drug dosages are, in particular instances, measured as injectable dosages.

Enhanced pK Profiles

The invention also preferably provides olanzapine compositions having a desirable pharmacokinetic profile when administered to mammalian subjects. The desirable pharmacokinetic profile of the olanzapine compositions preferably includes, but is not limited to: (1) a $C_{max}$ for olanzapine, when assayed in the plasma of a mammalian subject following administration, that is preferably greater than the $C_{max}$ for a non-nanoparticulate olanzapine formulation (e.g., Zyprexa®), administered at the same dosage; and/or (2) an AUC for olanzapine, when assayed in the plasma of a mammalian subject following administration, that is preferably greater than the AUC for a non-nanoparticulate olanzapine formulation (e.g., Zyprexa®), administered at the same dosage. The desirable pharmacokinetic profile, as used herein, is the pharmacokinetic profile measured after the initial injectable dose of olanzapine.

Conventional olanzapine (e.g., Zyprexa®), reaches peak plasma levels in 5-8 hours, and has a half-life of about 35 hours, depending on metabolism.

A preferred injectable olanzapine composition of the invention exhibits in comparative pharmacokinetic testing with a non-nanoparticulate olanzapine formulation of (e.g., Zyprexa®), administered at the same dosage, a $C_{max}$ which is at least about 50%, at least about 100%, at least about 200%, at least about 300%, at least about 400%, at least about 500%, at least about 600%, at least about 700%, at least about 800%, at least about 900%, at least about 1000%, at least about 1100%, at least about 1200%, at least about 1300%, at least about 1400%, at least about 1500%, at least about 1600%, at least about 1700%, at least about 1800%, or at least about 1900% greater than the $C_{max}$ exhibited by the non-nanoparticulate olanzapine formulation.

A preferred injectable olanzapine composition of the invention exhibits in comparative pharmacokinetic testing with a non-nanoparticulate olanzapine formulation (e.g., Zyprexa®), administered at the same dosage, an AUC which is at least about 25%, at least about 50%, at least about 75%, at least about 100%, at least about 125%, at least about 150%, at least about 175%, at least about 200%, at least about 225%, at least about 250%, at least about 275%, at least about 300%, at least about 350%, at least about 400%, at least about 450%, at least about 500%, at least about 550%, at least about 600%, at least about 750%, at least about 700%, at least about 750%, at least about 800%, at least about 850%, at least about 900%, at least about 950%, at least about 1000%, at least about 1050%, at least about 1100%, at least about 1150%, or at least about 1200% greater than the AUC exhibited by the non-nanoparticulate olanzapine formulation.

Combination Pharmacokinetic Profile Compositions

In yet another embodiment of the invention, a first nanoparticulate olanzapine composition providing a desired pharmacokinetic profile is co-administered, sequentially administered, or combined with at least one other olanzapine composition that generates a desired different pharmacokinetic profile. More than two olanzapine compositions can be co-administered, sequentially administered, or combined. While the first olanzapine composition has a nanoparticulate particle size, the additional one or more olanzapine compositions can be nanoparticulate, solubilized, or have a microparticulate particle size.

The second, third, fourth, etc., olanzapine compositions can differ from the first, and from each other, for example: (1) in the effective average particle sizes of olanzapine; or (2) in the dosage of olanzapine. Such a combination composition can reduce the dose frequency required.

If the second olanzapine composition has a nanoparticulate particle size, then preferably the olanzapine particles of the second composition have at least one surface stabilizer associated with the surface of the drug particles. The one or more surface stabilizers can be the same as or different from the surface stabilizer(s) present in the first olanzapine composition.

Preferably where co-administration of a "fast-acting" formulation and a "longer-lasting" formulation is desired, the two formulations are combined within a single composition, for example a dual-release composition.

A. Olanzpine Compositions

The invention provides compositions comprising nanoparticulate olanzapine particles and at least one surface stabilizer. The surface stabilizers are preferably adsorbed to or associated with the surface of the olanzapine particles. Surface stabilizers useful herein do not chemically react with the olanzapine particles or itself. Preferably, individual molecules of the surface stabilizer are essentially free of intermolecular cross-linkages. The compositions can comprise two or more surface stabilizers.

The present invention also includes nanoparticulate olanzapine compositions together with one or more non-toxic physiologically acceptable carriers, adjuvants, or vehicles, collectively referred to as carriers. The compositions can be formulated for parenteral injection (e.g., intravenous, intramuscular, or subcutaneous).

Olanzapine can be in a crystalline phase, an amorphous phase, a semi-crystalline phase, a semi-amorphous phase, or a mixtures thereof.

Illustrative but not limiting compositions comprise, based on % w/w:

| | |
|---|---|
| Olanzapine | 5-50% |
| Surface stabilizer | 0.1-50% |
| preservatives (Optional) | 0.05-0.25% |
| pH adjusting agent | pH about 6 to about 7 |
| water for injection | q.s. |

1. Surface Stabilizers

The choice of a surface stabilizer for olanzapine is non-trivial and required experimentation to realize a desirable formulation. Combinations of more than one surface stabilizer can be used in the invention. Useful surface stabilizers which can be employed in the invention include, but are not limited to, known organic and inorganic pharmaceutical excipients. Such excipients include various polymers, low molecular weight oligomers, natural products, and surfactants. Surface stabilizers include nonionic, ionic, anionic, cationic, and zwitterionic surfactants.

Preferred surface stabilizers include, but are not limited to, a polysorbate, such as Tween 80, benzalkonium chloride, and combinations thereof.

Representative examples of useful surface stabilizers include but are not limited to Low viscosity hydroxypropyl cellulose (HPC or HPC-SL); hydroxypropyl methyl cellulose (HPMC); hydroxymethyl cellulose (HMC); ethycellulose; povidone; Pluronics; sodium deoxycholate; PEG-Phospholipids; Tyloxapol and other approved tritons, polyvinylpyrrolidone, sodium lauryl sulfate, dioctylsulfosuccinate, gelatin, casein, lecithin (phosphatides), dextran, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters (e.g., the commercially available Tweens® such as e.g., Tween 20® and Tween 80® (ICI Speciality Chemicals)); polyethylene glycols (e.g., Carbowaxs 3550® and 934® (Union Carbide)), polyoxyethylene stearates, colloidal silicon dioxide, phosphates, carboxymethylcellulose calcium, carboxymethylcellulose sodium, methylcellulose, hydroxyethylcellulose, hydroxypropylmethylcellulose phthalate, noncrystalline cellulose, magnesium aluminium silicate, triethanolamine, polyvinyl alcohol (PVA), 4-(1,1,3,3-tetramethylbutyl)-phenol polymer with ethylene oxide and formaldehyde (also known as tyloxapol, superione, and triton), poloxamers (e.g., Pluronics F68® and F108®, which are block copolymers of ethylene oxide and propylene oxide); poloxamines (e.g., Tetronic 908®, also known as Poloxamine 908®, which is a tetrafunctional block copolymer derived from sequential addition of propylene oxide and ethylene oxide to ethylenediamine (BASF Wyandotte Corporation, Parsippany, N.J.)); Tetronic 1508® (T-1508) (BASF Wyandotte Corporation), Tritons X-200®, which is an alkyl aryl polyether sulfonate (Rohm and Haas); Crodestas F-110®, which is a mixture of sucrose stearate and sucrose distearate (Croda Inc.); p-isononylphenoxypoly-(glycidol), also known as Olin-lOG® or Surfactant 10-G® (Olin Chemicals, Stamford, Conn.); Crodestas SL-40® (Croda, Inc.); and SA90HCO, which is $C_{18}H_{37}CH_2(CON(CH_3)-CH_2(CHOH)_4(CH_2OH)_2$ (Eastman Kodak Co.); decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl-β-D-glucopyranoside; n-heptyl β-D-thioglucoside; n-hexyl β-D-glucopyranoside; nonanoyl-N-methylglucamide; n-noyl β-D-glucopyranoside; octanoyl-N-methylglucamide; n-octyl-β-D-glucopyranoside; octyl β-D-thioglucopyranoside; PEG-derivatized phospholipid, PEG-derivatized cholesterol, PEG-derivatized cholesterol derivative, PEG-derivatized vitamin A, PEG-derivatized vitamin E, lysozyme, random copolymers of vinyl pyrrolidone and vinyl acetate, and the like.

Povidone Polymers

In one embodiment of the invention, a povidone polymer is utilized as a surface stabilizer. Povidone polymers for injectable compositions preferably have a molecular weight of less than about 40,000 daltons. Povidone polymers, also known as polyvidon(e), povidonum, PVP, and polyvinylpyrrolidone, are sold under the trade names Kollidon® (BASF Corp.) and Plasdone® (ISP Technologies, Inc.). They are polydisperse macromolecular molecules, with a chemical name of 1-ethenyl-2-pyrrolidinone polymers and 1-vinyl-2-pyrrolidinone polymers. Povidone polymers are produced commercially as a series of products having mean molecular weights ranging from about 10,000 to about 700,000 daltons. To be useful as a surface modifier for a drug compound to be administered to a mammal, the povidone polymer must have a molecular weight of less than about 40,000 daltons, as a molecular weight of greater than 40,000 daltons would have difficulty clearing the body.

Povidone polymers are prepared by, for example, Reppe's process, comprising: (1) obtaining 1,4-butanediol from acetylene and formaldehyde by the Reppe butadiene synthesis; (2) dehydrogenating the 1,4-butanediol over copper at 200° to form γ-butyrolactone; and (3) reacting γ-butyrolactone with ammonia to yield pyrrolidone. Subsequent treatment with acetylene gives the vinyl pyrrolidone monomer. Polymerization is carried out by heating in the presence of $H_2O$ and $NH_3$. See The Merck Index, 10$^{th}$ Edition, page 1106 (Merck & Co., Rahway, N.J., 1983).

The manufacturing process for povidone polymers produces polymers containing molecules of unequal chain length, and thus different molecular weights. The molecular weights of the molecules vary about a mean or average for each particular commercially available grade. Because it is difficult to determine the polymer's molecular weight directly, the most widely used method of classifying various molecular weight grades is by K-values, based on viscosity measurements. The K-values of various grades of povidone polymers represent a function of the average molecular weight, and are derived from viscosity measurements and calculated according o Fikentscher's formula.

The weight-average of the molecular weight, Mw, is determined by methods that measure the weights of the individual molecules, such as by light scattering. Table 1 provides molecular weight data for several commercially available povidone polymers, all of which are soluble.

TABLE 1

| Povidone | K-Value | Mv (Daltons)** | Mw (Daltons)** | Mn (Daltons)** |
| --- | --- | --- | --- | --- |
| Plasdone C-15 ® | 17 ± 1 | 7,000 | 10,500 | 3,000 |
| Plasdone C-30 ® | 30.5 ± 1.5 | 38,000 | 62,500* | 16,500 |
| Kollidon 12 PF ® | 11-14 | 3,900 | 2,000-3,000 | 1,300 |
| Kollidon 17 PF ® | 16-18 | 9,300 | 7,000-11,000 | 2,500 |
| Kollidon 25 ® | 24-32 | 25,700 | 28,000-34,000 | 6,000 |

*Because the molecular weight is greater than 40,000 daltons, this povidone polymer is not useful as a surface stabilizer for a drug compound to be administered parenterally (i.e., injected).
**Mv is the viscosity-average molecular weight, Mn is the number-average molecular weight, and Mw is the weight average molecular weight. Mw and Mn were determined by light scattering and ultra-centrifugation, and Mv was determined by viscosity measurements.

Based on the data provided in Table 1, exemplary preferred commercially available povidone polymers for injectable compositions include, but are not limited to, Plasdone C-15®, Kollidon 12 PF®, Kollidon 17 PF®, and Kollidon 25®.

Cationic Surface Stabilizers

Depending upon the desired method of administration, bioadhesive formulations of nanoparticulate olanzapine can be prepared by selecting one or more cationic surface stabilizers that impart bioadhesive properties to the resultant composition. Useful cationic surface stabilizers are described below.

Examples of useful cationic surface stabilizers include, but are not limited to, polymers, biopolymers, polysaccharides, cellulosics, alginates, phospholipids, and nonpolymeric compounds, such as zwitterionic stabilizers, poly-n-methylpyridinium, anthryul pyridinium chloride, cationic phospholipids, chitosan, polylysine, polyvinylimidazole, polybrene, polymethylmethacrylate trimethylammoniumbromide bromide (PMMTMABr), hexyldesyltrimethylammonium bromide (HDMAB), polyvinylpyrrolidone-2 dimethylaminoethyl methacrylate dimethyl sulfate, 1,2 Dipalmitoyl-sn-Glycero-3-Phosphoethanolamine-N-[Amino(Polyethylene Glycol)2000] (sodium salt) (also known as DPPE-PEG (2000)-Amine Na) (Avanti Polar Lipids, Alabaster, Ala.), Poly(2-methacryloxyethyl trimethylammonium bromide) (Polysciences, Inc., Warrington, Pa.) (also known as SI 001), poloxamines such as Tetronic 908®, also known as Poloxamine 908®, which is a tetrafunctional block copolymer derived from sequential addition of propylene oxide and ethylene oxide to ethylenediamine (BASF Wyandotte Corporation, Parsippany, N.J.), lysozyme, long-chain polymers such as alginic acid, carrageenan (FMC Corp.), and POLYOX (Dow, Midland, Mich.).

Other useful cationic stabilizers include, but are not limited to, cationic lipids, sulfonium, phosphonium, and quarternary ammonium compounds, such as stearyltrimethylammonium chloride, benzyl-di(2-chloroethyl)ethylammonium bromide, coconut trimethyl ammonium chloride or bromide, coconut methyl dihydroxyethyl ammonium chloride or bromide, decyl triethyl ammonium chloride, decyl dimethyl hydroxyethyl ammonium chloride or bromide, $C_{12-15}$dimethyl hydroxyethyl ammonium chloride or bromide, coconut dimethyl hydroxyethyl ammonium chloride or bromide, myristyl trimethyl ammonium methyl sulphate, lauryl dimethyl benzyl ammonium chloride or bromide, lauryl dimethyl (ethenoxy)$_4$ ammonium chloride or bromide, N-alkyl ($C_{12-18}$)dimethylbenzyl ammonium chloride, N-alkyl ($C_{14-18}$) dimethyl-benzyl ammonium chloride, N-tetradecylidmethyl-benzyl ammonium chloride monohydrate, dimethyl didecyl ammonium chloride, N-alkyl and ($C_{12-14}$) dimethyl 1-napthylmethyl ammonium chloride, trimethylammonium halide, alkyl-trimethylammonium salts and dialkyl-dimethylammonium salts, lauryl trimethyl ammonium chloride, ethoxylated alkyamidoalkyldialkylammonium salt and/or an ethoxylated trialkyl ammonium salt, dialkylbenzene dialkylammonium chloride, N-didecyldimethyl ammonium chloride, N-tetradecyldimethylbenzyl ammonium, chloride monohydrate, N-alkyl($C_{12-14}$) dimethyl 1-naphthylmethyl ammonium chloride and dodecyldimethylbenzyl ammonium chloride, dialkyl benzenealkyl ammonium chloride, lauryl trimethyl ammonium chloride, alkylbenzyl methyl ammonium chloride, alkyl benzyl dimethyl ammonium bromide, $C_{12}$, $C_{15}$, $C_{17}$ trimethyl ammonium bromides, dodecylbenzyl triethyl ammonium chloride, poly-diallyldimethylammonium chloride (DADMAC), dimethyl ammonium chlorides, alkyldimethylammonium halogenides, tricetyl methyl ammonium chloride, decyltrimethylammonium bromide, dodecyltriethylammonium bromide, tetradecyltrimethylammonium bromide, methyl trioctylammonium chloride (ALIQUAT 336™), POLYQUAT 10™, tetrabutylammonium bromide, benzyl trimethylammonium bromide, choline esters (such as choline esters of fatty acids), benzalkonium chloride, stearalkonium chloride compounds (such as stearyltrimonium chloride and Di-stearyldimonium chloride), cetyl pyridinium bromide or chloride, halide salts of quaternized polyoxyethylalkylamines, MIRAPOL™ and ALKAQUAT™ (Alkaril Chemical Company), alkyl pyridinium salts; amines, such as alkylamines, dialkylamines, alkanolamines, polyethylenepolyamines, N,N-dialkylaminoalkyl acrylates, and vinyl pyridine, amine salts, such as lauryl amine acetate, stearyl amine acetate, alkylpyridinium salt, and alkylimidazolium salt, and amine oxides; imide azolinium salts; protonated quaternary acrylamides; methylated quaternary polymers, such as poly [diallyl dimethylammonium chloride] and poly-[N-methyl vinyl pyridinium chloride]; and cationic guar.

Such exemplary cationic surface stabilizers and other useful cationic surface stabilizers are described in J. Cross and E. Singer, *Cationic Surfactants: Analytical and Biological Evaluation* (Marcel Dekker, 1994); P. and D. Rubingh (Editor), *Cationic Surfactants: Physical Chemistry* (Marcel Dekker, 1991); and J. Richmond, *Cationic Surfactants: Organic Chemistry*, (Marcel Dekker, 1990).

Nonpolymeric cationic surface stabilizers are any nonpolymeric compound, such as benzalkonium chloride, a carbonium compound, a phosphonium compound, an oxonium compound, a halonium compound, a cationic organometallic compound, a quarternary phosphorous compound, a pyridinium compound, an anilinium compound, an ammonium compound, a hydroxylammonium compound, a primary ammonium compound, a secondary ammonium compound, a tertiary ammonium compound, and quarternary ammonium compounds of the formula $NR_1R_2R_3R_4^{(+)}$. For compounds of the formula $NR_1R_2R_3R_4^{(+)}$:

(i) none of $R_1$-$R_4$ are $CH_3$;
(ii) one of $R_1$-$R_4$ is $CH_3$;
(iii) three of $R_1$-$R_4$ are $CH_3$;
(iv) all of $R_1$-$R_4$ are $CH_3$;
(v) two of $R_1$-$R_4$ are $CH_3$, one of $R_1$-$R_4$ is $C_6H_5CH_2$, and one of $R_1$-$R_4$ is an alkyl chain of seven carbon atoms or less;
(vi) two of $R_1$-$R_4$ are $CH_3$, one of $R_1$-$R_4$ is $C_6H_5CH_2$, and one of $R_1$-$R_4$ is an alkyl chain of nineteen carbon atoms or more;
(vii) two of $R_1$-$R_4$ are $CH_3$ and one of $R_1$-$R_4$ is the group $C_6H_5(CH_2)_n$, where n>1;
(viii) two of $R_1$-$R_4$ are $CH_3$, one of $R_1$-$R_4$ is $C_6H_5CH_2$, and one of $R_1$-$R_4$ comprises at least one heteroatom;
(ix) two of $R_1$-$R_4$ are $CH_3$, one of $R_1$-$R_4$ is $C_6H_5CH_2$, and one of $R_1$-$R_4$ comprises at least one halogen;
(x) two of $R_1$-$R_4$ are $CH_3$, one of $R_1$-$R_4$ is $C_6H_5CH_2$, and one of $R_1$-$R_4$ comprises at least one cyclic fragment;
(xi) two of $R_1$-$R_4$ are $CH_3$ and one of $R_1$-$R_4$ is a phenyl ring; or
(xii) two of $R_1$-$R_4$ are $CH_3$ and two of $R_1$-$R_4$ are purely aliphatic fragments.

Such compounds include, but are not limited to, behenalkonium chloride, benzethonium chloride, cetylpyridinium chloride, behentrimonium chloride, lauralkonium chloride, cetalkonium chloride, cetrimonium bromide, cetrimonium chloride, cethylamine hydrofluoride, chlorallylmethenamine chloride (Quaternium-15), distearyldimonium chloride (Quaternium-5), dodecyl dimethyl ethylbenzyl ammonium chloride(Quaternium-14), Quaternium-22, Quaternium-26, Quaternium-18 hectorite, dimethylaminoethylchloride hydrochloride, cysteine hydrochloride, diethanolammonium POE (10) oletyl ether phosphate, diethanolammonium POE (3)oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procainehydrochloride, cocobetaine, stearalkonium bentonite, stearalkoniumhectonite, stearyl trihydroxyethyl propylenediamine dihydrofluoride, tallowtrimonium chloride, and hexadecyltrimethyl ammonium bromide.

Most of these surface stabilizers are known pharmaceutical excipients and are described in detail in the *Handbook of Pharmaceutical Excipients*, published jointly by the American Pharmaceutical Association and The Pharmaceutical Society of Great Britain (The Pharmaceutical Press, 2000), specifically incorporated by reference.

The surface stabilizers are commercially available and/or can be prepared by techniques known in the art.

While applicants do not wish to be bound by theoretical mechanisms, it is believed that the stabilizer hinders the flocculation and/or agglomeration of the olanzapine particles by functioning as a mechanical or steric barrier between the particles, minimizing the close, interparticle approach necessary for agglomeration and flocculation.

2. Excipients

Exemplary preservatives include methylparaben (about 0.18% based on % w/w), propylparaben (about 0.02% based on % w/w), phenol (about 0.5% based on % w/w), and benzyl alcohol (up to 2% v/v). An exemplary pH adjusting agent is sodium hydroxide, and an exemplary liquid carrier is sterile water for injection. Other useful preservatives, pH adjusting agents, and liquid carriers are well-known in the art.

3. Nanoparticulate Olanzapine Particle Size

As used herein, particle size is determined on the basis of the weight average particle size as measured by conventional particle size measuring techniques well known to those skilled in the art. Such techniques include, for example, sedimentation field flow fractionation, photon correlation spectroscopy, light scattering, and disk centrifugation.

The compositions of the invention comprise olanzapine nanoparticles which have an effective average particle size of less than about 5 microns. In other embodiments of the invention, the olanzapine particles have a size of less than about 4900 nm, less than about 4800 nm, less than about 4700 nm, less than about 4600 run, less than about 4500 nm, less than about 4400 nm, less than about 4300 nm, less than about 4200 nm, less than about 4100 nm, less than about 4 microns, less than about 3900 nm, less than about 3800 nm, less than about 3700 nm, less than about 3600 nm, less than about 3500 nm, less than about 3400 nm, less than about 3300 nm, less than about 3200 nm, less than about 3100 nm, less than about 3 microns, less than about 2900 nm, less than about 2800 nm, less than about 2700 nm, less than about 2600 nm, less than about 2500 nm, less than about 2400 nm, less than about 2300 nm, less than about 2200 nm, less than about 2100 nm, less than about 2000 nm, less than about 1900 nm, less than less than about 1800 nm, less than about 1700 nm, less than about 1600 nm, less than about 1500 nm, less than about 1400 nm, less than about 1300 nm, less than about 1200 nm, less than about 1100 nm, less than about 1000 nm, less than about 900 nm, less than about 800 nm, less than about 700 nm, less than about 600 nm, less than about 500 nm, less than about 400 nm, less than about 300 nm, less than about 250 nm, less than about 200 nm, less than about 150 nm, less than about 140 nm, less than about 130 nm, less than about 120 nm, less than about 110 nm, less than about 100 nm, less than about 90 nm, less than about 80 nm, less than about 70 mm, less than about 60 nm, or less than about 50 nm, when measured by the above-noted techniques.

By "an effective average particle size of less than about 5 microns" it is meant that at least 50% of the nanoparticulate olanzapine particles have a weight average particle size of less than about 5 microns, when measured by the above-noted techniques. In other embodiments of the invention, at least about 70%, at least about 90%, at least about 95%, or at least about 99% of the nanoparticulate olanzapine particles have a particle size of less than the effective average, by weight, i.e., less than about 5 microns, less than about 4900 nm, less than less than about 4800 nm, less than about 4700 nm, etc. (as listed in the paragraph above).

If the nanoparticulate olanzapine composition is combined with a microparticulate olanzapine or non-olanzapine active agent composition, then such a composition is either solubilized or has an effective average particle size of greater than about 5 microns. By "an effective average particle size of greater than about 5 microns" it is meant that at least 50% of the microparticulate olanzapine or non-olanzapine active agent particles have a particle size of greater than about 5 microns, by weight, when measured by the above-noted techniques. In other embodiments of the invention, at least about 70%, at least about 90%, at least about 95%, or at least about 99%, by weight, of the microparticulate olanzapine or non-olanzapine active agent particles have a particle size greater than about 5 microns.

In the present invention, the value for D50 of a nanoparticulate olanzapine composition is the particle size below which 50% of the olanzapine particles fall, by weight. Similarly, D90 and D99 are the particle sizes below which 90% and 99%, respectively, of the olanzapine particles fall, by weight.

4. Concentration of Nanoparticulate Olanzapine and Surface Stabilizers

The relative amounts of olanzapine and one or more surface stabilizers can vary widely. The optimal amount of the individual components can depend, for example, upon the hydrophilic lipophilic balance (HLB), melting point, and the surface tension of water solutions of the stabilizer, etc.

The concentration of olanzapine can vary from about 99.5% to about 0.001%, from about 95% to about 0.1%, from about 90% to about 0.5%, or from about 5.0% to about 50%, by weight, based on the total combined dry weight of the olanzapine and at least one surface stabilizer, not including other excipients.

The concentration of the at least one surface stabilizer can vary from about 0.5% to about 99.999%, from about 5.0% to about 99.9%, from about 10% to about 99.5%, or from about 0.1 to about 50%, by weight, based on the total combined dry weight of the olanzapine and at least one surface stabilizer, not including other excipients.

5. Additional Active Agents

The invention encompasses the nanoparticulate olanzapine compositions of the invention formulated or co-administered with one or more non-olanzapine active agents. Methods of using such combination compositions are also encompassed by the invention. The non-olanzapine active agents can be present in a crystalline phase, an amorphous phase, a semi-crystalline phase, a semi-amorphous phase, or a mixture thereof.

The compound to be administered in combination with a nanoparticulate olanzapine composition of the invention can be formulated separately from the nanoparticulate olanzapine composition or co-formulated with the nanoparticulate olanzapine composition. Where a nanoparticulate olanzapine composition is co-formulated with a second active agent, the second active agent can be formulated in any suitable manner, such as immediate-release, rapid-onset, sustained-release, or dual-release form.

Such non-olanzapine active agents can be, for example, a therapeutic agent. A therapeutic agent can be a pharmaceutical agent, including a biologic. The active agent can be selected from a variety of known classes of drugs, including, for example, amino acids, proteins, peptides, nucleotides, anti-obesity drugs, central nervous system stimulants, carotenoids, corticosteroids, elastase inhibitors, anti-fungals, oncology therapies, anti-emetics, analgesics, cardiovascular agents, anti-inflammatory agents, such as NSAIDs and COX-2 inhibitors, anthelmintics, anti-arrhythmic agents, antibiotics (including penicillins), anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytics, sedatives (hypnotics and neuroleptics), astringents, alpha-adrenergic receptor blocking agents, beta-adrenoceptor blocking agents, blood products and substitutes, cardiac inotropic agents, contrast media, corticosteroids, cough suppressants (expectorants and mucolytics), diagnostic agents, diagnostic imaging agents, diuretics, dopaminergics (antiparkinsonian agents), haemostatics, immunological agents, lipid regulating agents, muscle relaxants, parasympathomimetics, parathyroid calcitonin and biphosphonates, prostaglandins, radio-pharmaceuticals, sex hormones (including steroids), anti-allergic agents, stimulants and anoretics, sympathomimetics, thyroid agents, vasodilators, and xanthines.

Examples of secondary active agents particularly useful in the compositions of the invention include, but are not limited to, antidepressants. Examples of classes of useful antidepressants include, but are not limited to, selective serotonin reuptake inhibitors (SSRIs), tricyclic antidepressants, and monoamine oxidase Inhibitors (MAOI's). Examples of antidepressants include, but are not limited to, citalopram (Celexa®), escitalopram HB (Lexapro®), fluoxetine hydrochloride (Prozac®), paroxetine (Paxil®), fluvoxamine (Luvox®), sertraline (Zoloft®), venlafaxine (Effexor®), amitriptyline (Elavil®), desipramine, nortriptyline, duloxetine (Cymbalta®), mirtazepine (Remeron®), phenelzine (Nardil®), tranylcypromine (Pamateg), nefazodone (Serzone®), trazodone, and bupropion (Wellbutrin®). A particularly useful antidepressant is fluoxetine (Prozac®).

B. Methods of Making Injectable Olanzapine Formulations

In another aspect of the invention there is provided a method of preparing the injectable nanoparticulate olanzapine formulations of the invention. The method comprises of one of the following methods: attrition, precipitation, evaporation, or combinations of these. Exemplary methods of making nanoparticulate compositions are described in U.S. Pat. No. 5,145,684. Methods of making nanoparticulate compositions are also described in U.S. Pat. No. 5,518,187 for "Method of Grinding Pharmaceutical Substances;" U.S. Pat. No. 5,718,388 for "Continuous Method of Grinding Pharmaceutical Substances;" U.S. Pat. No. 5,862,999 for "Method of Grinding Pharmaceutical Substances;" U.S. Pat. No. 5,665,331 for "Co-Microprecipitation of Nanoparticulate Pharmaceutical Agents with Crystal Growth Modifiers;" U.S. Pat. No. 5,662,883 for "Co-Microprecipitation of Nanoparticulate Pharmaceutical Agents with Crystal Growth Modifiers;" U.S. Pat. No. 5,560,932 for "Microprecipitation of Nanoparticulate Pharmaceutical Agents;" U.S. Pat. No. 5,543,133 for "Process of Preparing X-Ray Contrast Compositions Containing Nanoparticles;" U.S. Pat. No. 5,534,270 for "Method of Preparing Stable Drug Nanoparticles;" U.S. Pat. No. 5,510,118 for "Process of Preparing Therapeutic Compositions Containing Nanoparticles;" and U.S. Pat. No. 5,470,583 for "Method of Preparing Nanoparticle Compositions Containing Charged Phospholipids to Reduce Aggregation," all of which are specifically incorporated by reference.

Following milling, homogenization, precipitation, etc., the resultant nanoparticulate olanzapine composition can be utilized a liquid dosage formulation for injectable administration.

In one embodiment of the invention, the olanzapine particles are reduced to an effective average particle size of less than about 600 nm. Preferably, the effective average particle size of the nanoparticulate olanzapine is less than about 450 nm, more preferably less than about 300 nm, even more preferably less than about 250 nm, and most preferably less than about 100 nm. The pH of the liquid dispersion media is preferably maintained within the range of from about 3.0 to about 8.0, or about 5.0 to about 7.5, more preferably, at a pH of about 7.4, during the size reduction process. Preferably, the dispersion media used for the size reduction process is aqueous. However, any media in which olanzapine is poorly soluble and dispersible can be used as a dispersion media. Non-aqueous examples of dispersion media include, but are not limited to, aqueous salt solutions, safflower oil and solvents such as ethanol, t-butanol, hexane, and glycol.

Effective methods of providing mechanical force for particle size reduction of olanzapine include ball milling, media milling, and homogenization, for example, with a Microfluidizer® (Microfluidics Corp.). Ball milling is a low energy milling process that uses milling media, drug, stabilizer, and liquid. The materials are placed in a milling vessel that is rotated at optimal speed such that the media cascades and reduces the drug particle size by impaction. The media used must have a high density as the energy for the particle reduction is provided by gravity and the mass of the attrition media.

Media milling is a high energy milling process. Drug, stabilizer, and liquid are placed in a reservoir and recirculated in a chamber containing media and a rotating shaft/impeller. The rotating shaft agitates the media which subjects the drug to impaction and sheer forces, thereby reducing the drug particle size.

Homogenization is a technique that does not use milling media. Drug, stabilizer, and liquid (or drug and liquid with the stabilizer added after particle size reduction) constitute a process stream propelled into a process zone, which in the Microfluidizer® is called the Interaction Chamber. The product to be treated is inducted into the pump, and then forced out. The priming valve of the Microfluidizer® purges air out of the pump. Once the pump is filled with product, the priming valve is closed and the product is forced through the interaction chamber. The geometry of the interaction chamber produces powerful forces of sheer, impact, and cavitation which are responsible for particle size reduction. Specifically, inside the interaction chamber, the pressurized product is split into two streams and accelerated to extremely high velocities. The formed jets are then directed toward each other and collide in the interaction zone. The resulting product has very fine and uniform particle or droplet size. The Microfluidizer® also provides a heat exchanger to allow cooling of the product. U.S. Pat. No. 5,510,118, which is specifically incorporated by reference, refers to a process using a Microfluidizer® resulting in nanoparticulate particles.

Olanzapine can be added to a liquid medium in which it is essentially insoluble to form a premix. The concentration of the olanzapine in the liquid medium can vary from about 5 to about 60%, and preferably is from about 15 to about 50% (w/v), and more preferably about 20 to about 40%. The surface stabilizer can be present in the premix, it can be during particle size reduction, or it can be added to the drug dispersion following particle size reduction. The concentration of the surface stabilizer can vary from about 0.1 to about 50%, and preferably is from about 0.5 to about 20%, and more preferably from about 1 to about 10%, by weight.

The premix can be used directly by subjecting it to mechanical means to reduce the average olanzapine particle size in the dispersion to the desired size, preferably less than about 5 microns. It is preferred that the premix be used directly when a ball mill is used for attrition. Alternatively, olanzapine and the surface stabilizer can be dispersed in the liquid media using suitable agitation, e.g., a Cowles type mixer, until a homogeneous dispersion is observed in which there are no large agglomerates visible to the naked eye. It is preferred that the premix be subjected to such a premilling dispersion step when a recirculating media mill is used for attrition.

The mechanical means applied to reduce the olanzapine particle size conveniently can take the form of a dispersion mill. Suitable dispersion mills include a ball mill, an attritor mill, a vibratory mill, and media mills such as a sand mill and a bead mill. A media mill is preferred due to the relatively shorter milling time required to provide the desired reduction in particle size. For media milling, the apparent viscosity of the premix is preferably from about 100 to about 1000 centipoise, and for ball milling the apparent viscosity of the premix is preferably from about 1 up to about 100 centipoise. Such ranges tend to afford an optimal balance between efficient particle size reduction and media erosion but are in no way limiting The attrition time can vary widely and depends primarily upon the particular mechanical means and processing conditions selected. For ball mills, processing times of up to five days or longer may be required. Alternatively, processing times of less than 1 day (residence times of one minute up to several hours) are possible with the use of a high shear media mill.

The olanzapine particles must be reduced in size at a temperature which does not significantly degrade olanzapine. Processing temperatures of less than about 30° to less than about 40° C. are ordinarily preferred. If desired, the processing equipment can be cooled with conventional cooling equipment. Control of the temperature, e.g., by jacketing or immersion of the milling chamber with a cooling liquid, is contemplated. Generally, the method of the invention is conveniently carried out under conditions of ambient temperature and at processing pressures which are safe and effective for the milling process. Ambient processing pressures are typical of ball mills, attritor mills, and vibratory mills.

Grinding Media

The grinding media can comprise particles that are preferably substantially spherical in shape, e.g., beads, consisting essentially of polymeric resin or glass or Zirconium Silicate or other suitable compositions. Alternatively, the grinding media can comprise a core having a coating of a polymeric resin adhered thereon.

In general, suitable polymeric resins are chemically and physically inert, substantially free of metals, solvent, and monomers, and of sufficient hardness and friability to enable them to avoid being chipped or crushed during grinding. Suitable polymeric resins include crosslinked polystyrenes, such as polystyrene crosslinked with divinylbenzene; styrene copolymers; polycarbonates; polyacetals, such as Delrin® (E.I. du Pont de Nemours and Co.); vinyl chloride polymers and copolymers; polyurethanes; polyamides; poly(tetrafluoroethylenes), e.g., Teflon® (E.I. du Pont de Nemours and Co.), and other fluoropolymers; high density polyethylenes; polypropylenes; cellulose ethers and esters such as cellulose acetate; polyhydroxymethacrylate; polyhydroxyethyl acrylate; and silicone-containing polymers such as polysiloxanes and the like. The polymer can be biodegradable. Exemplary biodegradable polymers include poly(lactides), poly(glycolide) copolymers of lactides and glycolide, polyanhydrides, poly(hydroxyethyl methacylate), poly(imino carbonates), poly(N-acylhydroxyproline)esters, poly(N-palmitoyl hydroxyproline) esters, ethylene-vinyl acetate copolymers, poly(orthoesters), poly(caprolactones), and poly(phosphazenes). For biodegradable polymers, contamination from the media itself advantageously can metabolize in vivo into biologically acceptable products that can be eliminated from the body.

The grinding media preferably ranges in size from about 0.01 to about 3 mm. For fine grinding, the grinding media is preferably from about 0.02 to about 2 mm, and more preferably from about 0.03 to about 1 mm in size.

The polymeric resin can have a density from about 0.8 to about 3.0 g/cm$^3$.

In one embodiment of the invention, the olanzapine particles are made continuously. Such a method comprises continuously introducing olanzapine into a milling chamber, contacting the olanzapine with grinding media while in the chamber to reduce the olanzapine particle size, and continuously removing the nanoparticulate olanzapine from the milling chamber.

The grinding media can be separated from the milled nanoparticulate olanzapine using conventional separation techniques, in a secondary process such as by simple filtration, sieving through a mesh filter or screen, and the like. Other separation techniques such as centrifugation may also be employed. Alternatively, a screen can be utilized during the milling process to remove the grinding media following completion of particle size reduction.

Sterile Product Manufacturing

Development of injectable compositions requires the production of a sterile product. The manufacturing process of the present invention is similar to typical known manufacturing processes for sterile suspensions. A typical sterile suspension manufacturing process flowchart is as follows:

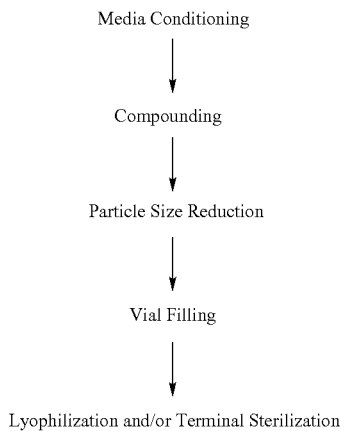

As indicated by the optional steps in parentheses, some of the processing is dependent upon the method of particle size reduction and/or method of sterilization. For example, media conditioning is not required for a milling method that does not use media. If terminal sterilization is not feasible due to chemical and/or physical instability, aseptic processing can be used.

C. Method of Treatment

Yet another aspect of the present invention provides a method of treating a mammal, including a human, of disorders of the central nervous system including, but not limited to psychiatric treatment. Such treatment comprises administering to the subject the injectable nanoparticulate olanzapine formulation of the invention. As used herein, the term "subject" is used to mean an animal, preferably a mammal, including a human or non-human. The terms patient and subject may be used interchangeably.

Examples of disorders that can be treated with olanzapine include, but are not limited to, schizophrenia and related psychoses, bipolar mania and/or bipolar disorder, seizures, obsessive/compulsive disorders, generalized anxiety disorder, post traumatic distress syndrome, extreme shyness, diabetic nerve pain, smoking cessation, and depression.

Particularly advantageous features of the present invention include that the pharmaceutical formulation of the invention exhibits a prolonged duration of action that can be controlled upon administration, and produces minimal or no pain or irritation upon administration. For example, compositions of the invention can provide efficacious levels of drug for up to about one week, from about two to about six weeks, or from about two to about twelve weeks. In addition, the injectable formulation of the invention can provide a high olanzapine concentration in a small volume to be injected. A general protocol for administration thereof comprises an intramuscular or subcutaneous bolus injection of olanzapine.

Conventional olanzapine (Zyprexa®) has a starting single evening dose of 10 mg. The usual maximum dose should be 20 mg. For treatment of psychoses, such as schizophrenia, the adult dosage is 5-10 mg/day initially, with a target dose of 10 mg/day within several days.

Olanzapine shows mesolimbic sensitivity, blocks conditioned avoidance at lower doses than those inducing catalepsy, substitutes for clozapine in a drug discrimination assay, produces a modest rise in prolactin, produces few extrapyramidal side effects, and reduces positive and negative symptoms of schizophrenia as efficaciously as clozapine. However, despite this 'atypical' profile, olanzapine has a weaker alpha-2 blockade than clozapine or risperidone. It has relatively high affinity for muscarinic, 5HT-2, and D1, D2 and D4 receptors. Trials suggest a good response in schizophrenia with few extrapyramidal side effects (EPSEs).

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents, or vehicles including water, ethanol, polyols (propyleneglycol, polyethylene-glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

The nanoparticulate compositions may also contain adjuvants such as preserving, wetting, emulsifying, and dispensing agents. Prevention of the growth of microorganisms can be ensured by various antibacterial and antifungal agents, such as parabens, chlorobutanol, phenol, sorbic acid, and the like. It may also be desirable to include isotonic agents, such as sugars, sodium chloride, and the like. Prolonged absorption of the injectable pharmaceutical form can be brought about by the use of agents delaying absorption, such as aluminum monostearate and gelatin.

One of ordinary skill will appreciate that effective amounts of olanzapine can be determined empirically and can be employed in pure form or, where such forms exist, in pharmaceutically acceptable salt, ester, or prodrug form. Actual dosage levels of olanzapine in the nanoparticulate compositions of the invention may be varied to obtain an amount of olanzapine that is effective to obtain a desired therapeutic response for a particular composition and method of administration. The selected dosage level therefore depends upon the desired therapeutic effect, the route of administration, the potency of the administered olanzapine, the desired duration of treatment, and other factors.

Dosage unit compositions may contain such amounts of such submultiples thereof as may be used to make up the daily dose. It will be understood, however, that the specific dose level for any particular patient will depend upon a variety of factors: the type and degree of the cellular or physiological response to be achieved; activity of the specific agent or composition employed; the specific agents or composition employed; the age, body weight, general health, sex, and diet of the patient; the time of administration, route of administration, and rate of excretion of the agent; the duration of the treatment; drugs used in combination or coincidental with the specific agent; and like factors well known in the medical arts.

The following examples are given to illustrate the present invention. It should be understood, however, that the spirit and scope of the invention is not to be limited to the specific conditions or details described in these examples but should only be limited by the scope of the claims that follow. All references identified herein, including U.S. patents, are hereby expressly incorporated by reference.

EXAMPLE 1

The purpose of this example is to illustrate the procedure for identifying a suitable nanoparticulate formulation of olanzapine.

The study can be conducted by screening eleven surface stabilizers to identify the most suitable stabilizer for parenteral administration of olanzapine. The dispersions can be formulated at 40% solids to 2.4% surface stabilizer.

TABLE 2

| Surface Stabilizer |
| --- |
| Plasdone C15 ® (polyvinylpyrrolidone) |
| Kollidon 17PF ® |
| (a polyvinylpyrrolidone polymer) |
| Povidone K30 ® |
| (a polyvinylpyrrolidone polymer) |
| Tyloxapol |
| Pluronic F68 ® |
| (a high molecular weight polyoxyalkylene ether) |
| Pluronic F108 ® |
| (a high molecular weight polyoxyalkylene ether) |
| Tween 80 ® |
| (a polyoxyethylene sorbitan fatty acid ester) |
| dioctylsulfosuccinate (CAS No. 577-11-7; aka Docusate Sodium) |
| B20-5000 ® |
| (a triblock copolymer surface modifier) |
| B20-5000-sulfonated |
| (a triblock copolymer surface modifier) |
| lecithin (CAS No. 8002-43-5) |
| Povidone K30 ® and Pluronic F108 ® |

Such combinations may produce stable dispersions of differing nanoparticulate size that will have differing durations of action when administered. Preclinical and clinical studies will identify the optimum formulation and size associated with the desired prolonged duration of action.

EXAMPLE 2

The purpose of this example was to prepare a nanoparticulate formulation 10 of olanzapine.

The particle size of olanzapine drug crystals was first measured prior to incorporation into a nanoparticulate formulation. The particle size, as measured using a Horiba LA 910 particle size analyzer (Horiba Instruments, Irvine, Calif.), was a mean of 137.08 microns, and a D90 of less than 335.59 microns. See FIG. 1.

An aqueous dispersion of 10% olanzapine (Camida LLC, Newark, N.J.), combined with 1% Tween 80, 0.1% benzalkonium chloride, and 20% dextrose, was milled in a NanoMill® 0.01 (Elan Drug Delivery), along with 500 micron PolyMill® grinding media (Dow Chemical) (50-89% media load). The mixture was milled at a speed of 1009-5500 rpms, at a temperature of 5-10° C., for about 30 min.

Figure 2:
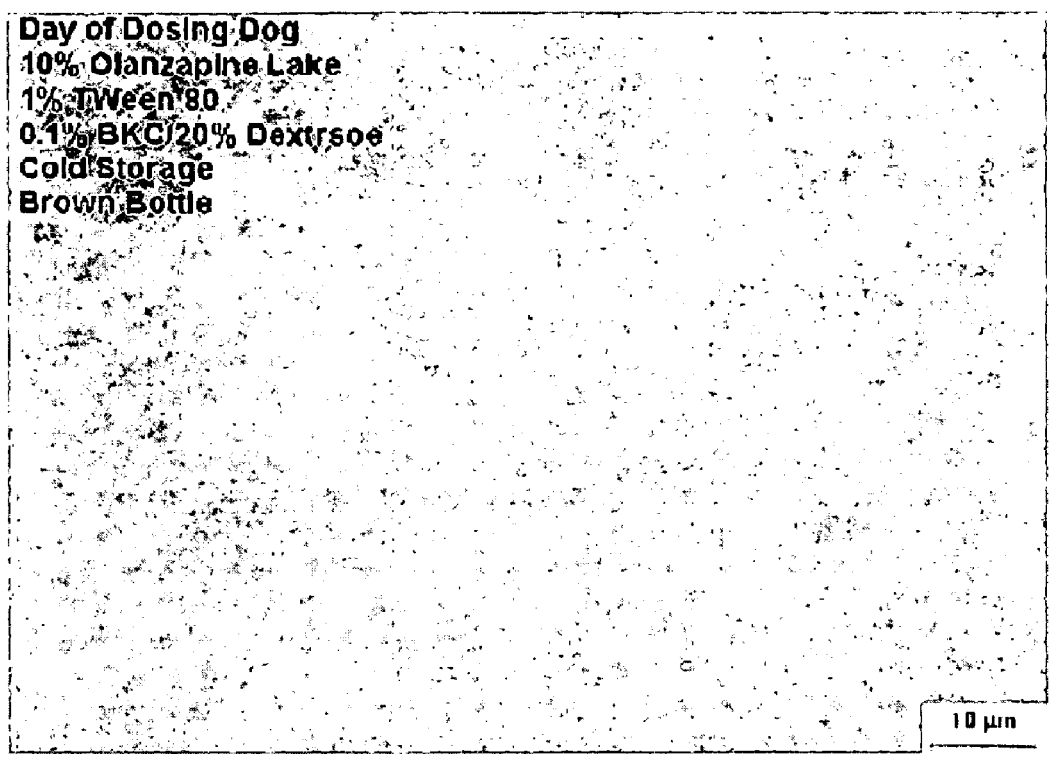
FIG. 2: Shows an electron micrograph of a milled nanoparticulate olanzapine formulation.

Following milling, the particle size of the milled olanzapine particles was measured, in deionized distilled water, using a Horiba LA 910 particle size analyzer. The median milled olanzapine particle size was 347 nm, with a mean size of 606 nm, a D90 of 1.28 microns, and a D83 of less than 1 micron. See FIG. 2.

EXAMPLE 3

The purpose of this example was to prepare a nanoparticulate formulation of olanzapine.

An aqueous dispersion of 30% olanzapine (Camida LLC, Newark, N.J.), combined with 2.5% Tween 80, was milled in a NanoMill® 0.01 (Elan Drug Delivery), along with 500 micron PolyMill® grinding media (Dow Chemical) (50-89% media load). The mixture was milled at a speed of 1009-5500 rpms, at a temperature of 5-10° C., for about 30 min.

Figure 3:
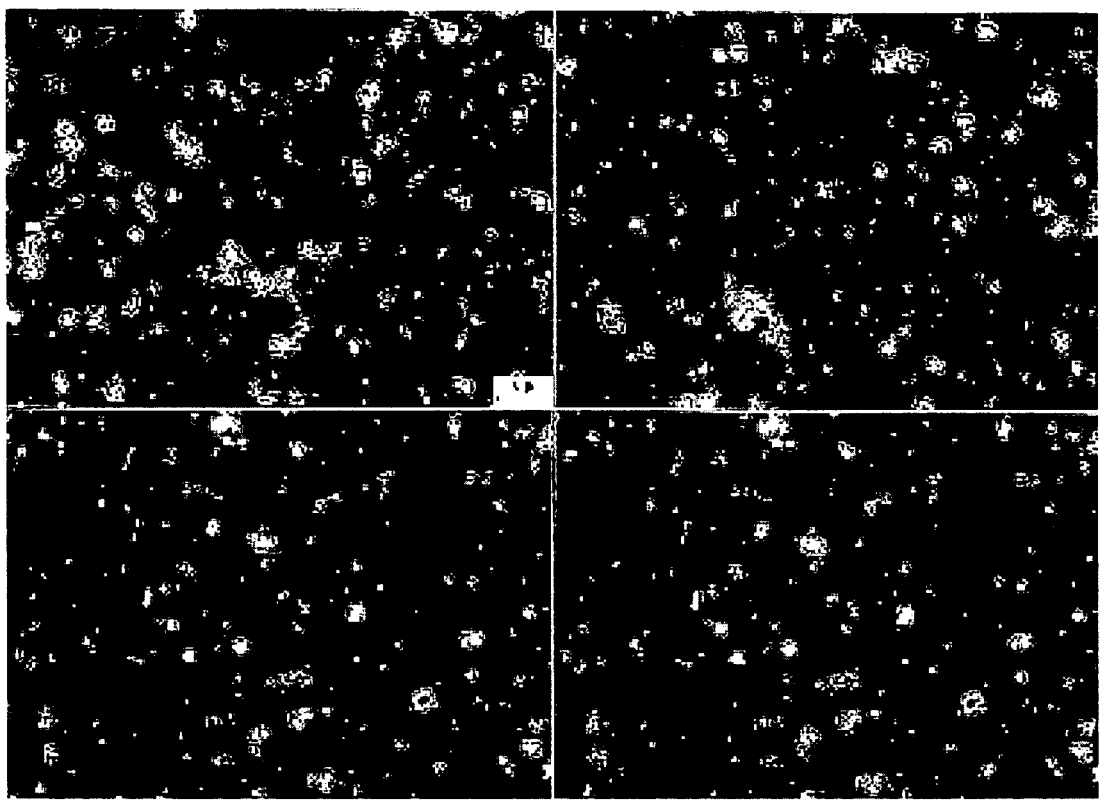
FIG. 3: Shows an electron micrograph of a milled nanoparticulate olanzapine formulation.

Following milling, the particle size of the milled olanzapine particles was measured, in deionized distilled water, using a Horiba LA 910 particle size analyzer. The median milled olanzapine particle size was 990 nm, with a mean size of 1.136 nm, a D90 of 2.07 microns, and a D50 of less than 1 micron. See FIG. 3.

EXAMPLE 4

The purpose of this example was to determine the in vivo characteristics of the nanoparticulate olanzapine formulation prepared in Example 2.

Figure 4:
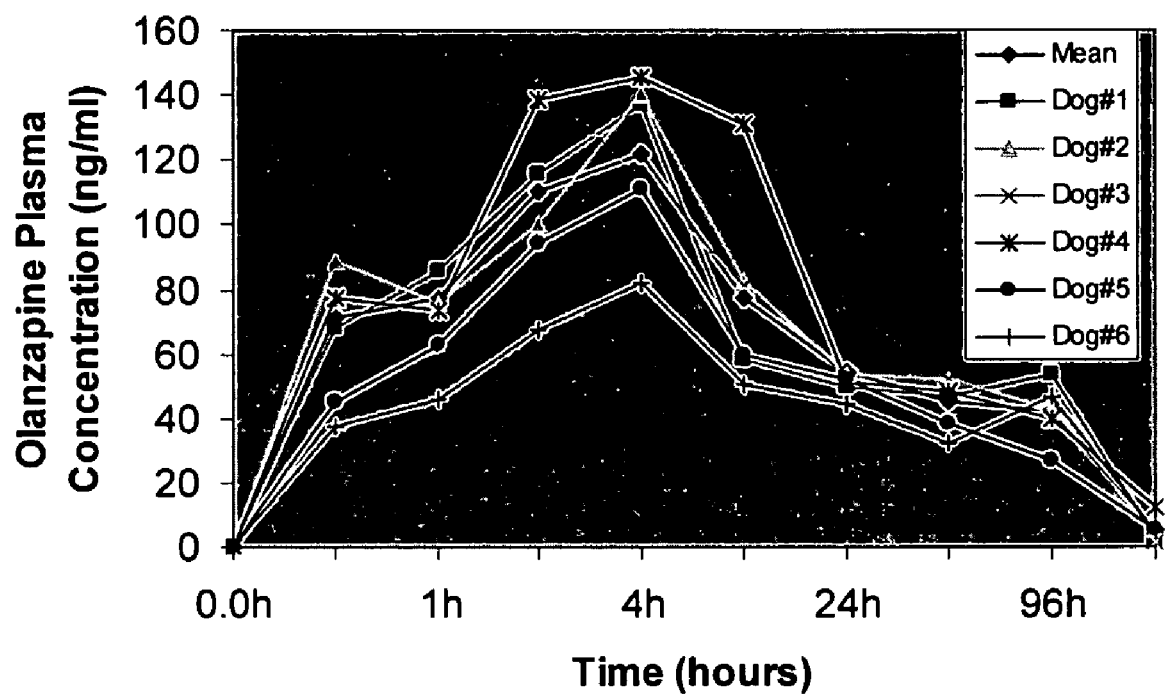
FIG. 4: Graphically shows the plasma concentration (ng/mL) of olanazpine over a six hour time period following intramuscular administration to six male dogs of a nanoparticulate olanzapine formulation.
Figure 5:
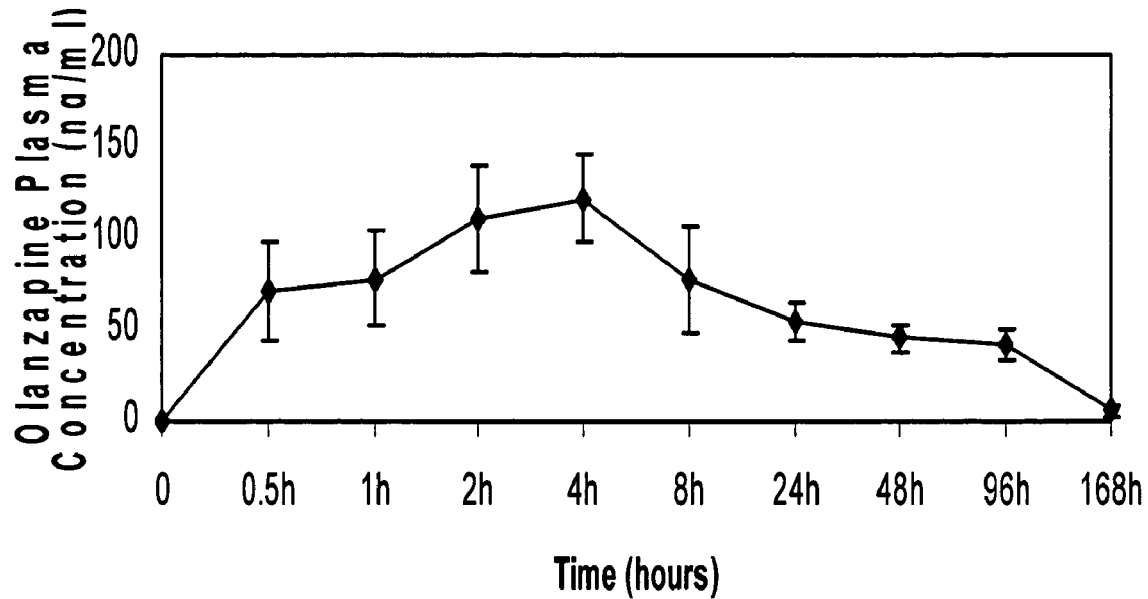
FIG. 5: Graphically shows the plasma concentration (ng/mL) of olanazpine over a six hour time period following intramuscular administration to six male dogs of a nanoparticulate olanzapine formulation.

An in vivo study, utilizing male beagle dogs, was conducted to determine the therapeutic levels of olanazapine present in vivo over a period of time following intramuscular (IM) administration of the nanoparticulate olanazapine formulation prepared in Example 2. Six dogs were given a single intramuscular dose of 10 mg/kg (about 100 mg/animal), which is about 10× the daily dose in humans. Blood samples were taken at t=0, 0.5, 1, 2, 4, 8, 24, and 49 hours post administration, and 4, 7, 14, and 28 days post administration. The plasma concentration (ng/ml) over a 168 hr period is shown in FIG. 4. As shown in FIG. 4, therapeutic levels of olanzapine, of 5 to 22 ng/ml, were present in vivo for over a 168 hr period. FIG. 5 further demonstrates that for all animals dosed, therapeutic levels of olanzapine, of 5 to 22 ng/ml, were present in vivo for over a 168 hr period.

In addition to demonstrating that the injectable olazapine formulations of the invention produce measurable and detectable levels of drug in the plasma for more than seven days following administration, this example further demonstrates: (1) that the olanzapine formulation prepared as in Example 2 is syringeable with a 23 gauge needle; and (2) that the olanzapine formulation prepared as in Example 2 is well tolerated by mammals.

It will be apparent to those skilled in the art that various modifications and variations can be made in the methods and compositions of the present invention without departing from the spirit or scope of the invention. Thus, it is intended that the present invention cover the modifications and variations of this invention provided they come within the scope of the appended claims and their equivalents.

What we claim is:

1. An injectable nanoparticulate olanzapine composition comprising: (a) olanzapine nanoparticles having an effective average particle size that results in a therapeutic efficacy of about one week or greater; (b) at least one surface stabilizer; and (c) a pharmaceutically acceptable carrier, wherein said effective average particle size is between about 300 nm and about 5000 nm.

2. The composition of claim 1, wherein the composition is administered via intramuscular or subcutaneous injection so as to form a depot.

3. The composition of claim 2, wherein the depot releases the olanzapine at therapeutic levels for a period of time from about two to about six weeks.

4. The composition of claim 2, wherein the depot releases the olanzapine at therapeutic levels for a period of time from about two to about twelve weeks.

5. The composition of claim 2, wherein the depot releases the olanzapine at therapeutic levels for a period of time selected from one week to about two weeks, from about one week to about three weeks, from about one week to about four weeks, from about one week to about five weeks, from about one week to about six weeks, from about one week to about seven weeks, from about one week to about eight weeks, from about one week to about nine weeks, from about one week to about ten weeks, from about one week to about eleven weeks, or from about one week to about twelve weeks.

6. The composition of claim 1, wherein the olanzapine is selected from the group consisting of a crystalline phase, an amorphous phase, a semi-crystalline phase, a semi-amorphous phase, and mixtures thereof.

7. The composition of claim 1, wherein the effective average particle size of the olanzapine particles is about 4900 nm, about 4800 nm, about 4700 nm, about 4600 nm, about 4500 nm, about 4400 nm, about 4300 nm, about 4200 nm, about 4100 nm, about 4 microns, about 3900 nm, about 3800 nm, about 3700 nm, about 3600 nm, about 3500 nm, about 3400 mm, about 3300 nm, about 3200 nm, about 3100 nm, about 3 microns, about 2900 mm, about 2800 nm, about 2700 nm, about 2600 nm, about 2500 nm, about 2400 nm, about 2300 nm, about 2200 nm, about 2100 nm, about 2000 nm, about 1900 nm, about 1800 nm, about 1700 nm, about 1600 nm, about 1500 nm, about 1400 nm, about 1300 nm, about 1200 nm, about 1100 nm, about 1000 nm, about 900 nm, about 800 nm, about 700 nm, about 600 nm, about 500 nm, about 400 nm, or about 300 nm.

8. The composition of claim 1, wherein: (a) the olanzapine is present in an amount from about 99.5% to about 0.001%, from about 95% to about 0.1%, from about 90% to about 0.5%, and from about 5.0% to about 50%, by weight, based on the total combined weight of the olanzapine and at least one surface stabilizer, not including other excipients; and (b) the at least one surface stabilizer is present in an amount selected from the group consisting of from about 0.5% to about 99.999% by weight, from about 5.0% to about 99.9% by weight, from about 10% to about 99.5%, or from about 0.1 to about 50%, by weight, based on the total combined dry weight of the olanzapine and at least one surface stabilizer, not including other excipients.

9. The composition of claim 1, wherein the surface stabilizer is a non-ionic surface stabilizer, an anionic surface stabilizer, a cationic surface stabilizer, or a zwitterionic surface stabilizer.

10. The composition of claim 1, wherein at least one surface stabilizer is cetyl pyridinium chloride, gelatin, casein, phosphatides, dextran, glycerol, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers, polyoxyethylene castor oils, polyoxyethylene sorbitan fatty acid esters, polyethylene glycols, dodecyl trimethyl ammonium bromide, polyoxyethylene stearates, colloidal silicon dioxide, phosphates, sodium dodecylsulfate, carboxymethylcellulose calcium, hydroxypropyl celluloses, hypromellose, carboxymethylcellulose sodium, methylcellulose, hydroxyethylcellulose, hypromello se phthalate, non-crystalline cellulose, magnesium aluminum silicate, triethanolamine, polyvinyl alcohol, polyvinylpyrrolidone, 4-(1,1,3,3-tetramethylbutyl)-phenol polymer with ethylene oxide and formaldehyde, poloxamers; poloxamines, a charged phospho lipid, dioctylsulfosuccinate, dialkylesters of sodium sulfosuccinic acid, sodium lauryl sulfate, alkyl aryl polyether sulfonates, mixtures of sucrose stearate and sucrose distearate, p-isononylphenoxypoly-(glycidol), decanoyl-N-methylglucamide; n-decyl-β-D-glucopyranoside; n-decyl β-D-maltopyranoside; n-dodecyl β-D-glucopyranoside; n-dodecyl β-D-maltoside; heptanoyl-N-methylglucamide; n-heptyl- β-D-glucopyrano side; n-heptyl β-D-thioglucoside; n-hexyl β-D-glucopyranoside; nonanoyl-N-methylglucamide; n-noyl β-D-glucopyranoside; octanoyl-N-methylglucamide; n-octyl- β-D-glucopyranoside; octyl β-D-thioglucopyranoside; lysozyme, PEG-phospholipid, PEG-cholesterols, PEG-vitamin A, random copolymers of vinyl acetate and vinyl pyrrolidone, cationic polymers, cationic biopolymers, cationic polysaccharides, cationic cellulosics, cationic alginates, cationic nonpolymeric compounds, cationic phospho lipids, cationic lipids, polymethylmethacrylate trimethylammonium bromide, sulfonium compounds, polyvinylpyrrolidone-2-dimethylaminoethyl methacrylate dimethyl sulfate, hexadecyltrimethyl ammonium bromide, phosphonium compounds, quarternary ammonium compounds, benzyl-di(2-chloroethyl)ethylammonium bromide, coconut trimethyl ammonium chloride, coconut trimethyl ammonium bromide, coconut methyl dihydroxyethyl ammonium chloride, coconut methyl dihydroxyethyl ammonium bromide, decyl triethyl ammonium chloride, decyl dimethyl hydroxyethyl ammonium chloride, decyl dimethyl hydroxyethyl ammonium chloride bromide, $C_{12-15}$dimethyl hydroxyethyl ammonium chloride, $C_{12-15}$dimethyl hydroxyethyl ammonium chloride bromide, coconut dimethyl hydroxyethyl ammonium chloride, coconut dimethyl hydroxyethyl ammonium bromide, myristyl trimethyl ammonium methyl sulphate, lauryl dimethyl benzyl ammonium chloride, lauryl dimethyl benzyl ammonium bromide, lauryl dimethyl (ethenoxy)$_4$ ammonium chloride, lauryl dimethyl (ethenoxy)$_4$ ammonium bromide, N-alkyl ($C_{12-18}$)dimethylbenzyl ammonium chloride, N-alkyl ($C_{14-18}$) dimethyl-benzyl ammonium chloride, N-tetradecylidmethylbenzyl ammonium chloride monohydrate, dimethyl didecyl ammonium chloride, N-alkyl and ($C_{12-14}$) dimethyl 1-napthylmethyl ammonium chloride, trimethylammonium halide, alkyl-trimethylammonium salts, dialkyl-dimethylammonium salts, lauryl trimethyl ammonium chloride, ethoxylated alkyamidoalkyldialkylammonium salt, an ethoxylated trialkyl ammonium salt, dialkylbenzene dialkylammonium chloride, N-didecyldimethyl ammonium chloride, N-tetradecyldimethylbenzyl ammonium, chloride monohydrate, N-alkyl($C_{12-14}$) dimethyl 1-naphthylmethyl ammonium chloride, dodecyldimethylbenzyl ammonium chloride, dialkyl benzenealkyl ammonium chloride, lauryl trimethyl ammonium chloride, alkylbenzyl methyl ammonium chloride, alkyl benzyl dimethyl ammonium bromide, $C_{12}$ trimethyl ammonium bromides, $C_{15}$ trimethyl ammonium bromides, $C_{12}$ trimethyl ammonium bromides, dodecylbenzyl triethyl ammonium chloride, poly-diallyldimethylammonium chloride (DADMAC), dimethyl ammonium chlorides, alkyldimethylammonium halogenides, tricetyl methyl ammonium chloride, decyltrimethylammonium bromide, dodecyltriethylammonium bromide, tetradecyltrimethylammonium bromide, methyl trioctylammonium chloride, Polyquaternium-10 (POLYQUAT 10™), tetrabutylammonium bromide, benzyl trimethylammonium bromide, choline esters, benzalkonium chloride, stearalkonium chloride compounds, cetyl pyridinium bromide, cetyl pyridinium chloride, halide salts of quaternized polyoxyethylalkylamines, Polyquaternium-11 (MIRAPOL™), stearyl -dimethylbenzylammonium chloride (ALKAQUAT™), alkyl pyridinium salts; amines, amine salts, amine oxides, imide azolinium salts, protonated quaternary acrylamides, methylated quaternary polymers, or cationic guar.

11. The composition of claim 1, comprising a surface stabilizer selected from the group consisting of a polysorbate, benzalkonium chloride, dextrose, and a combination thereof.

12. The composition of claim 1, further comprising at least one additional olanzapine composition having an effective average particle size which is different than the effective average particle size of the olanzapine composition of claim 1.

13. The composition of claim 1, additionally comprising one or more non-olanzapine active agents.

14. The composition of claim 13, wherein at least one non-olanzapine agent is an antidepressant.

15. The composition of claim 14, wherein the antidepressant is fluoxetine.

16. The composition of claim 1, wherein the composition is syringeable with a 23 gauge needle.

17. The composition of claim 1, wherein the effective average particle size of the olanzapine particles is less than 4900 nm, less than 4800 nm, less than 4700 nm, less than 4600 nm, less than 4500 nm, less than 4400 nm, less than 4300 mm, 4200 nm, less than 4100 nm, less than 4 microns, less than 3900 nm, less than 3800 nm, less than 3700 nm, less than 3600 nm, less than 3500 nm, less than 3400 mm, less than 3300 nm, less than 3200 nm, less than 3100 nm, less than 3 microns, less than 2900 mm, less than 2800 nm, less than 2700 nm, less than 2600 nm, less than 2500 nm, less than 2400 nm, less than 2300 nm, less than 2200 nm, less than 2100 nm, less than 2000 nm, less than 1900 nm, less than 1800 nm, less than 1700 nm, less than 1600 nm, less than 1500 nm, less than 1400 nm, less than 1300 nm, less than 1200 nm, less than 1100 nm, less than 1000 nm, less than 900 nm, less than 800 nm, less than 700 nm, less than 600 nm, less than 500 nm, or less than 400 nm.

* * * * *

UNITED STATES PATENT AND TRADEMARK OFFICE
CERTIFICATE OF CORRECTION

| | | |
|---|---|---|
| PATENT NO. | : 7,910,577 B2 | Page 1 of 1 |
| APPLICATION NO. | : 11/274887 | |
| DATED | : March 22, 2011 | |
| INVENTOR(S) | : Liversidge et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1415 days.

Signed and Sealed this
Ninth Day of August, 2011

David J. Kappos
*Director of the United States Patent and Trademark Office*